United States Patent [19]

Degischer et al.

[11] 4,317,916

[45] Mar. 2, 1982

[54] PROCESS FOR PRODUCING N-SUBSTITUTED-N-ACETYL-2,6-DIALKYL-ANILINES

[75] Inventors: Gerhard Degischer, Füllinsdorf; Werner Angst, Muttenz, both of Switzerland

[73] Assignee: Ciba-Geigy Corporation, Ardsley, N.Y.

[21] Appl. No.: 183,871

[22] Filed: Sep. 4, 1980

Related U.S. Application Data

[63] Continuation-in-part of Ser. No. 30,574, Apr. 16, 1979, abandoned.

[51] Int. Cl.³ .................... C07C 102/00; C07C 67/00
[52] U.S. Cl. ........................................ 560/43; 564/143
[58] Field of Search .......................... 564/143; 560/43

[56] References Cited

U.S. PATENT DOCUMENTS

| | | | |
|---|---|---|---|
| 3,937,730 | 2/1976 | Vogel et al. | 564/143 |
| 3,952,056 | 4/1976 | Vogel et al. | 564/210 |
| 4,008,066 | 2/1977 | Moser | 564/143 |

OTHER PUBLICATIONS

Handbook of Chemistry and Physics, 49th ed., 1968, p. F-85.

*Primary Examiner*—Arthur P. Demers
*Attorney, Agent, or Firm*—Karl F. Jorda

[57] ABSTRACT

An improved process for producing N-substituted N-acetyl-2,6-dialkylanilines of the formula

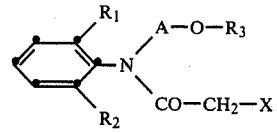

in which $R_1$ and $R_2$ independently of one another are each methyl or ethyl, A is a 1,2-ethylene group which can be substituted by 1 or 2 methyl groups, or a 2-oxo-1,2-ethylene group which can be substituted by 1 or 2 methyl groups, $R_3$ is an alkyl group having 1 to 3 carbon atoms, and X represents chlorine or an alkyl group having 1 to 3 carbon atoms, is disclosed, which process comprises reacting a N-substituted-2,6-dialkylaniline of the formula

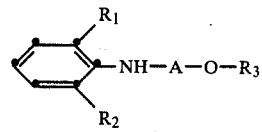

in which $R_1$, $R_2$, $R_3$ and A have the meaning given above with an acetyl chloride of the formula

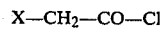

in which X has the meaning given above, in an excess of said acetyl chloride as solvent.

The N-substituted-N-acetyl-2,6-dialkylanilines of the above formula can be used for protecting plants from being infected by phytopathogenic microorganisms.

8 Claims, No Drawings

PROCESS FOR PRODUCING N-SUBSTITUTED-N-ACETYL-2,6-DIALKYL-ANILINES

This is a continuation-in-part application of application Ser. No. 30,574, filed Apr. 16, 1979, now abandoned.

The present invention relates to an improved process for producing N-substituted-N-acetyl-2,6-dialkylanilines of the formula I

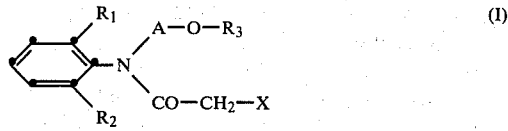

in which $R_1$ and $R_2$ independently of one another are each methyl or ethyl, A is a 1,2-ethylene group which can be substituted by 1 or 2 methyl groups, or a 2-oxo-1,2-ethylene group which can be substituted by 1 or 2 methyl groups, $R_3$ is an alkyl group having 1 to 3 carbon atoms, and X represents chlorine or an alkyl group having 1 to 3 carbon atoms, by reacting an N-substituted-2,6-dialkylaniline of the formula II

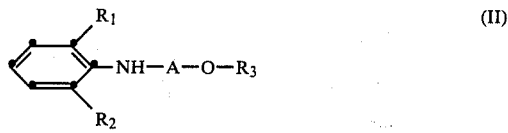

in which $R_1$, $R_2$, $R_3$ and A are as defined under the formula I, with an acetyl chloride of the formula III $$X-CH_2-CO-Cl \qquad (III)$$

in which X has the meaning given above.

The N-substituted-N-acetyl-2,6-dialkylanilines of the formula I have a pronounced action against phytopathogenic microorganisms, and are therefore used for protecting cultivated plants from being infected by phytopathogenic microorganisms. N-Substituted-N-acetyl-2,6-dialkylanilines of the formula I and their application are described for example in the U.S. Pat. Nos. 3,952,056, 3,937,730 and 4,206,228.

The method of producing N-substituted-N-acetyl-2,6-dialkylanilines of the formula I by reacting the corresponding N-substituted-2,6-dialkylanilines of the formula II with an acetyl chloride of the formula III is known. The reaction can be performed both in the absence and in the presence of inorganic or organic bases, such as sodium hydroxide, sodium carbonate, N,N-dimethylaniline and triethylamine. In carrying out the acetylation in the presence of aqueous inorganic bases, there is however required a large excess of acetyl chloride since a considerable part of the acetyl chloride is lost as a result of hydrolysis. This is on the one hand uneconomical and on the other hand undesirable on account of the ecological problems created, because the acid formed as a result of hydrolysis has to be removed from the waste liquor. This disadvantage of the use of a large excess of acetyl chloride can indeed be avoided by using organic bases, but in this case the respective amine hydrochloride formed has to be separated and the corresponding amine regenerated, a factor giving rise to additional expenditure.

While some acylation reactions can be performed in the absence of a base and in the absence of a solvent the reaction of an N-substituted-2,6-dialkylaniline of the formula II with an acetyl chloride of the formula III in the absence of a base always needs the presence of an inert solvent. If no solvent is present there is obtained a dark and highly viscous product which is difficult to handle and from which the desired product can only be isolated in very poor yields.

The performance of the reaction of an N-substituted-2,6-dialkylaniline of the formula II with an acetyl chloride of the formula III in the absence of a base in an inert solvent has the advantage that the hydrogen chloride formed during the reaction can be immediately separated in gaseous form. Since however the acetyl chloride is used, for economical reasons, essentially in an equimolar amount, long reaction times are necessary for the complete carrying out of the reaction and for the complete separation of the hydrogen chloride. It is as a rule necessary to heat the reaction mixture for several hours at a temperature of 90° to 110° C., in consequence of which secondary reactions, such as the splitting-off of ether and the formation of resinous by-products, are promoted. The yield of active substance is reduced as a result of these secondary reactions.

The processes mentioned in the foregoing are uneconomical by virtue of the disadvantages associated with them. It is therefore the object of the present invention to provide a process by which the N-substituted-N-acetyl-2,6-dialkylanilines of the formula I can be produced, in a simple and economical manner, in good yields on a commercial scale.

It has been found that N-substituted-N-acetyl-2,6-dialkylanilines of the formula I can be produced in excellent yields and with an excellent degree of purity by performing the reaction of N-substituted-2,6-dialkylanilines of the formula II with an acetyl chloride of the formula III in excess acetyl chloride of the formula III as solvent. The improved process according to the invention therefore comprises reacting the N-substituted-2,6-dialkylaniline of the formula II with an acetyl chloride of the formula III in the presence of excess acetyl chloride of the formula III as solvent, distilling off the excess acetyl chloride of the formula III, washing the formed N-substituted-N-acetyl-2,6-dialkylaniline of the formula I with water until neutral, and subsequently drying the product obtained.

The acetyl chloride of the formula III is used according to the invention in an amount of 2 to 20 mols, preferably 4 to 8 mols, per mol of N-substituted-2,6-dialkylaniline of the formula II. The reaction is advantageously performed in the temperature range of 70° C. to the reflux temperature of the reaction mixture, preferably at the reflux temperature of the reaction mixture.

The washing of the product obtained after the excess chloroacetyl chloride has been distilled off can be carried out with water at 50° to 110° C. It is advantageous to repeat the washing operation several times. It is also advantageous to add to the washing water an amount of alkali, particularly sodium hydroxide or potassium hydroxide, sufficient to bring the pH value of the water to 4 to 10. The product is subsequently dried, optionally after further washing with pure water, by heating at 100° to 120° C. in vacuo.

The process according to the invention can be performed either batchwise or continuously.

The process is performed batchwise advantageously by introducing the N-substituted-2,6-dialkylaniline of the formula II into the boiling acetyl chloride of the formula III, and distilling off the excess chloroacetyl chloride in vacuo after completion of the reaction.

In carrying out the process continuously, it is advantageous to introduce simultaneously the acetyl chloride of the formula III and the N-substituted-2,6-dialkylaniline of the formula II, at the reaction temperature, into the reaction vessel, and directly afterwards to concentrate the mixture in vacuo. The continous method of carrying out the process can be advantageously performed in a cascade reactor having 2 to 4 stages, or in a falling film reactor.

The hydrogen chloride formed during the reaction is separated in gaseous form, and can be compressed and fed into steel cylinders, or dissolved in water to form concentrated hydrochloric acid, or processed by oxidation into chlorine.

Among the N-substituted-2,6-dialkylanilines of the formula II which are used as starting materials those are preferred in which A represents a 1,2-ethylene group, a 1-methyl-1,2-ethylene group or a 1-methyl-2-oxo-1,2-ethylene group and $R_3$ is methyl. Particularly preferred starting materials of the formula III are N-(1'-methyl-2'-methoxyäthyl)-2-ethyl-6-methylaniline and N-(1'-methoxycarbonylethyl)-2,6-dimethylaniline. Among the acetyl chlorides of the formula III chloroacetyl chloride and methoxyacetyl chloride are preferred.

It is a particular advantage of the process according to the invention that the contamination of the environment with harmful substances is reduced to a minimum. The products obtained by the process according to the invention are very pure and the yield of the products is excellent. Since the reaction of N-substituted-2,6-dialkylanilines of the formula II with acetyl chlorides of the formula III proceeds very rapidly the residence time of the reactants in the reactor can be kept short and consequently the size of the reactor for the production of a given amount of product can be kept relatively small. In consequence of the possibility of using the acetyl chloride of the formula III again in the reaction, losses of substances are avoided. A further advantage of the process according to the invention is finally that the quantity ratio of the reactants can be varied within very wide limits without the quality of the final product being disadvantageously affected.

It is therefore possible by the process according to the invention to produce the N-substituted-N-acetyl-2,6-dialkylanilines of the formula I in a simple manner and in excellent yield and degree of purity.

The process according to the invention is further illustrated by the Examples which follow.

EXAMPLE 1

1356 g (12 mols) of chloroacetyl chloride is placed into a 3-liter three-necked flask provided with stirrer, dropping funnel and condenser, and heated to boiling. There is then added dropwise 207 g (1 mol) of N-(2'-methoxy-1'-methylethyl)-2-ethyl-6-methylaniline at such a rate that the solution always remains uniformly boiling and evolves gas. After the addition of N-(2'-methoxy-1'-methylethyl)-2-ethyl-6-methylaniline, the excess of chloroacetyl chloride is distilled off in a rotary evaporator at a pressure of 15 Torr. The crude product thus obtained is washed in a separating funnel with 200 ml of water, with the pH value of the washing water being adjusted to 8 by the addition of 30% sodium hydroxide solution. After separation of the aqueous phase, the product is firstly washed twice again with water, and then dried for 30 minutes at 110° C. and 15 Torr. The yield is 273.8 g (96.6% of theory) of N-(2'-methoxy-1'-methylethyl)-N-chloroacetyl-2-ethyl-6-methylaniline.

EXAMPLE 2

868 g (8 mols) of methoxyacetyl chloride is placed into a 2-liter three-necked flask provided with stirrer, dropping funnel and condenser, and heated to boiling. There is then added dropwise 165,6 g (0,8 mol) of N-(1'-methoxycarbonylethyl)-2,6-dimethylaniline at such a rate that the solution always remains uniformly boiling and evolves gas. After the addition of N-(1'-methoxycarbonylethyl)-2,6-dimethylaniline, the excess of methoxyacetyl chloride is distilled off in a rotary evaporator at a pressure of 15 Torr. The crude product thus obtained is washed at 80° C. with 100 ml of water with the pH of the washing water being adjusted to 4 by addition of 1N sodium hyroxide. After separation of the aqueous phase, the product is firstly washed twice again with warm water, and then dried for 1 hour at 110° C. and 15 Torr. The yield is 217.3 g (97,2% of theory) of N-(1'-methoxycarbonylethyl)-N-methoxyacetyl-2,6-dimethylaniline.

What is claimed is:

1. In a process for producing N-substituted-N-acetyl-2,6-dialkylanilines of the formula I

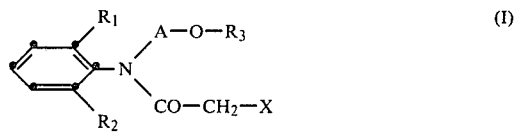

in which $R_1$ and $R_2$ independently of one another are each methyl or ethyl, A is a 1,2-ethylene group which can be substituted by 1 or 2 methyl groups, or a 2-oxo-1,2-ethylene group which can be substituted by 1 or 2 methyl groups, $R_3$ is an alkyl group having 1 to 3 carbon atoms, and X represents chlorine or an alkoxy group having 1 to 3 carbon atoms, by reacting an N-substituted-2,6-dialkylaniline of the formula II

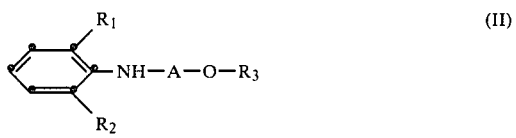

in which $R_1$, $R_2$, $R_3$ and A are as defined under the formula I, with an acetyl chloride of the formula III

in which X is as defined under formula I, the improvement which comprises reacting the N-substituted-2,6-dialkylaniline of the formula II with the acetyl chloride of the formula III in the presence of excess acetyl chloride of the formula III as solvent, distilling off the excess acetyl chloride of the formula III, washing the formed N-substituted-N-acetyl-2,6-dialkylaniline of the formula I with water until neutral, and subsequently drying the product.

2. A process according to claim 1, wherein 2 to 20 mols of acetyl chloride of the formula III are used per mol of N-substituted-2,6-dialkylaniline of the formula II.

3. A process according to claim 1, wherein 4 to 8 mols of acetyl chloride of the formula III are used per mol of N-substituted-2,6-dialkylaniline of the formula II.

4. A process according to claim 1, wherein the reaction of N-substituted-2,6-dialkylaniline of the formula II with the acetyl chloride of the formula III is performed in the temperature range of 70° C. to the reflux temperature of the reaction mixture.

5. A process according to claim 1, wherein the reaction of N-substituted-2,6-dialkylaniline of the formula II with the acetyl chloride of the formula III is performed at the reflux temperature of the reaction mixture.

6. A process according to claim 1, wherein the N-substituted-N-acetyl-2,6-dialkylaniline of the formula I, obtained after removal by distillation of the excess acetyl chloride of the formula III, is washed at 50° to 100° C. with water.

7. A process according to claim 1, wherein there is added to the washing water an amount of alkali sufficient to bring the pH value of the water to 4 to 10.

8. A process according to claim 6 wherein there is added to the washing water an amount of alkali sufficient to bring the pH value of the water to 8 to 12.

* * * * *